Aug. 10, 1971 B. L. COBIA Plant Pat. 3,054

MILKWEED PLANT FAMILY

Filed March 13, 1969

INVENTOR
Barnell L. Cobia

By Roger L. Martin
Attorney

MILKWEED PLANT FAMILY

Filed March 13, 1969 2 Sheets-Sheet 2

INVENTOR
Barnell L. Cobia

By Roger L. Martin
Attorney

United States Patent Office

Plant Pat. 3,054
Patented Aug. 10, 1971

3,054

MILKWEED PLANT FAMILY

Barnell L. Cobia, Winter Garden, Fla., assignor to
B. L. Cobia, Inc., Winter Garden, Fla.

Filed Mar. 13, 1969, Ser. No. 808,025
Int. Cl. A01h 5/00
U.S. Cl. Plt.—88 1 Claim

ABSTRACT OF THE DISCLOSURE

A new plant variety of the milkweed family closely resembles the Hoya carnosa compacta variety in structural appearance but is distinguishable from this variety by a more compact growth habit, leaf blades which are distinctively variegated and by certain color characteristics.

The invention relates to a new and distinct plant variety of the milkweed (Asclepiadaceae) family. The new variety has been developed from a sport that appeared as a bud variation on a cultivated plant specimen of the Hoya carnosa compacta variety and has been named the Hoya carnosa compacta Mauna Loa by the inventor.

Plant specimens of the Hoya carnosa compacta variety have become popular in the foliage plant market and with the natural preference that the public has for plant specimens which have variegated leaves, a principal objective of the invention has been to develop a new plant variety which is structurally similar in appearance to the Hoya carnosa compacta variety but which is nevertheless distinguishable from the latter by variegated leaf blade characteristics. This objective has been fully realized by the invention as will be apparent from the plant description contained herein.

The sport was discovered on a plant specimen of the Hoya carnosa compacta variety which was under cultivation at a nursery at Winter Garden, Fla., and the new variety has been asexually reproduced at the same nursery by the propagation of stem cuttings taking from the sport.

The new plant variety is distinguishable from the Hoya carnosa compacta variety by the distinctive characteristics enumerated below and is distinguishable from other antecedents and known related varieties by a growth habit which provides specimens of the new variety which are structurally closely similar in appearance to plant specimens of the Hoya carnosa compacta variety but which are nevertheless distinguishable therefrom by the following distinctive characteristics:

(1) A more compact growth habit.
(2) Lighter appearing stems which in color are characterized by hues which predominantly range from pink to orange yellow in fully matured stems.
(3) Lighter appearing petioles which in color are characterized by hues which predominantly range from olive to yellow green in fully matured leaves.
(4) Variegated leaf blades which at the upper epidermis side are distinctively characterized by a green border area that surrounds an albino center field which has green blotches that are lighter in color than in the border area and tend to concentrate along the surrounding border area, and which at the lower epidermis side are distinctively characterized by a field with green blotches that tend to concentrate along the margins of the leaf blade.
(5) An inflorescence with a peduncle which characteristically is grayish red and/or moderate red, with pedicels that are characteristically dark pink in color, and with sepals that are characteristically moderate red and/or grayish red.

The accompanying drawings serve by color photographic means to illustrate the new variety and wherein.

Figure 1:
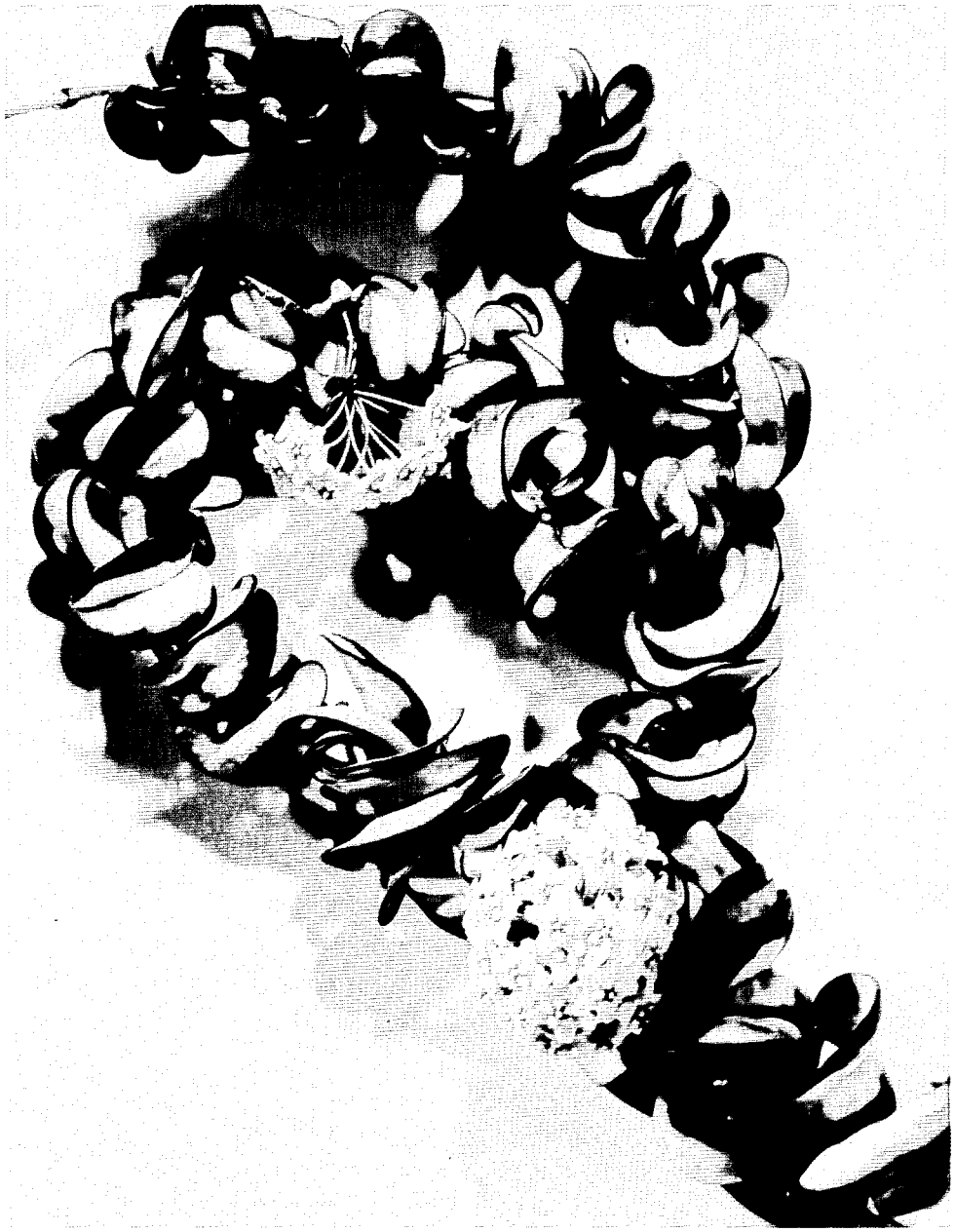
FIG. 1 shows a plant specimen which is in bloom.
Figure 2:
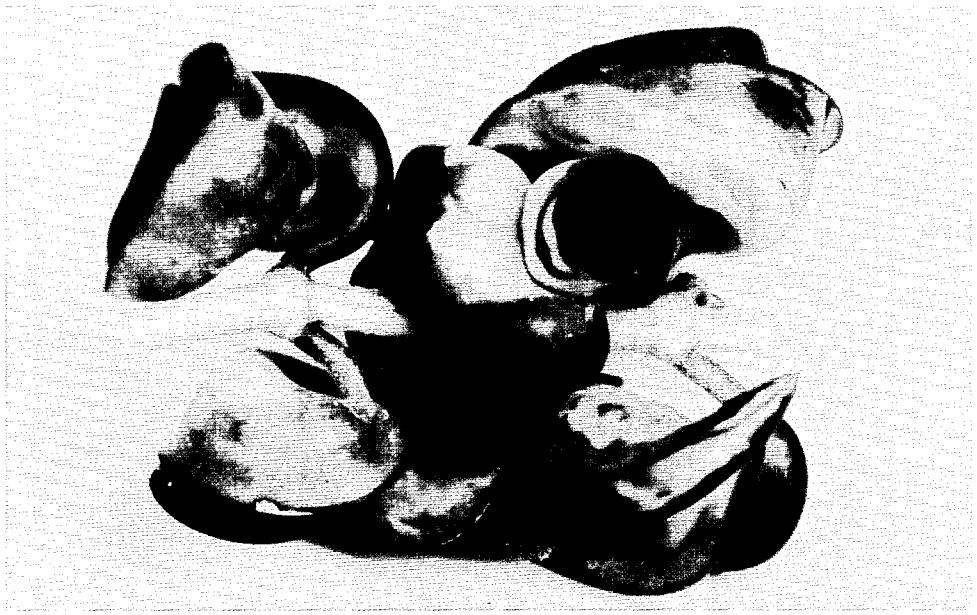
FIG. 2 is an enlarged photograph of a stem section.
Figure 3:
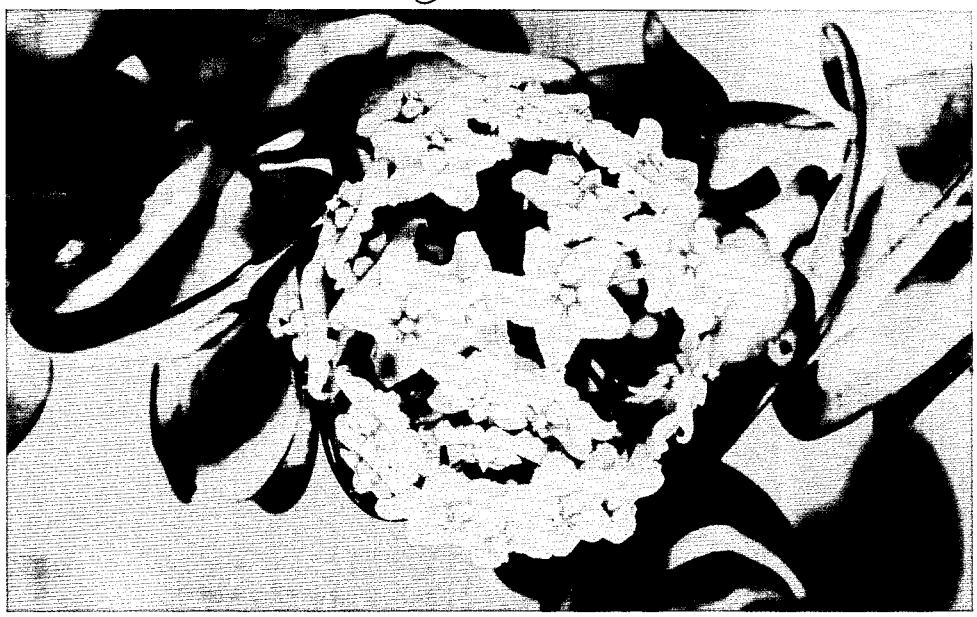
FIG. 3 is an enlarged photograph showing a bloom.

The following is a detailed description of the new variety and is based on observations of well fertilized specimens which were grown in the Central Florida area under 85% shaded nursery conditions and where temperatures range from about 60° F. to about 85° F. during the winter months and from about 75° F. to about 95° F. during the summer months. Except where general terms of ordinary dictionary significance are obviously used, color terminology and color designations reported herein are in accord with the ISCC-NBS method of designating colors as described in the U.S. Department of Commerce, National Bureau of Standards, Circular 553, entitled "The ISCC-NBS Method of Designating Colors and a Dictionary of Color Names" with the color designations having been derived through interpretation of Munsell Color Notations obtained by comparing plant specimens with color specimens in the current Neighboring Hues Edition of the Munsell Book of Color, published by Munsell Color Company, Inc. of Baltimore, Md. and to which the reported color notations (Munsell Hue Munsell Value/Munsell Chroma) are referenced.

*Plant description*

Name: Hoya carnosa compacta Mauna Loa.
Origin or Parentage: Hoya carnosa compacta.
Classification:
(*A*) *Botanic.*—Milkweed (Asclepiadaceae) family.
(*B*) *Commercial.*—Foliage plant.
Form: Semisucculent, tropical, twining vine type perennial evergreen with some branching.
Stems:
(*A*) *Botanic.*—Milkweed (Asclepiadaceae) family.
(*B*) *Commercial.*—Foliage plant.
(*C*) *Size.*—(1) Diameter: usually 3–6 mm. at full maturity. (2) Internode Length: characteristically shorter than in parent variety and thereby providing a more compact growth habit in appearance and with the internode length usually 15–30 mm. at full maturity.
(*D*) *Color.*—Lighter appearing than in parent variety and characterized by hues which predominantly range from pink to orange yellow in fully matured stems. Commonly light-moderate pink (2.5 R 8/4), (5 R 8/4), light-moderate yellowish pink (2.5 YR 8/4), (5 YR 8/4) and/or pale orange yellow (7.5 YR 8/4), (10 YR 8/4) in fully matured stems. Strong pink (2.5 R 7/8), moderate pink (5 R 7/6), dark pink (2.5 R 6/6) and/or moderate red (2.5 R 4/8) being common in immature stems.
Leaves:
(*A*) *General.*—Simple extipulate.
(*B*) *Arrangement.*—Opposite.
(*C*) *Margins.*—Entire.
(*D*) *Venation.*—Pinnate.
(*E*) *Shape.*—(1) General: ovate. (2) Leaf apices: acute with acuminate tendencies. (3) Leaf bases: cordate.
(*F*) *Petioles.*—(1) General: herbaceous, fleshy. (2) Texture: copious long hairs. (3) Size: (a) Diameter—usually 1.5–3 mm. in fully matured leaves. (b) Length—usually 5–10 mm. in fully matured leaves. (4) Color: lighter appearing in fully matured leaves than in parent variety and characterized in color by hues which predominantly range from olive to yellow green in fully matured leaves. Commonly moderate olive (5 Y 4/4), light olive (10 Y 5/6), (7.5 Y 5/6), light-moderate greenish yellow (10 Y 8/6), light-brilliant-moderate-strong greenish yellow (2.5 GY 8/8), brilliant yellow green (5 GY 8/8), strong yellow green (5 GY 8/6) in fully matured leaves. Moderate olive brown (2.5 Y 4/2), (2.5 Y 3/2), (2.5 Y 4/4), moderate olive (5 Y 4/4) and/or light olive (5 Y 5/6) being ordinary in leaves of less than full maturity.

(*G*) *Leaf blades.*—(1) General: semisucculent and variegated with curled, folded blade characteristics of parent variety. (2) Texture: (a) Upper epidermis—slightly pubescent in immature leaves and becoming glabrous with smooth waxy surface. (b) Lower epidermis—moderately pubescent and glaucous. (3) Size: (a) Length—usually 35–65 mm. in fully matured leaves. (b) Width (max.)—usually 20–40 mm. in fully matured leaves. (4) Color: (a) Upper epidermis—variegated and distinctively characterized by a green border area that surrounds an albino center field which has blotches that tend to concentrate along the surrounding border area and which are lighter in color than in the border area. (1) Green border area: commonly moderate olive green (7.5 GY 3/4), (7.5 GY 4/4), (7.5 GY 4/6), moderate yellow green (5 GY 5/6), (7.5 GY 5/6) and/or dark yellowish green (10 GY 4/4), (10 GY 4/6). (2) Center field background: commonly light yellow green (2.5 GY 9/4), greenish white (5 GY 9/1), pale yellow green (10 Y 9/2), (2.5 GY 9/2), (5 GY 9/2), yellowish white-pale yellow (7.5 Y 9/2), pale greenish yellow (7.5 Y 9/4), pale greenish yellow (7.5 Y 9/4), (10 Y 9/4), and/or light greenish yellow (7.5 Y 9/6). (3) Center field blotches: commonly moderate yellow green (2.5 GY 7/6), (5 GY 7/6), (7.5 GY 7/6), light yellow green (2.5 GY 8/6), (5 GY 8/6), and/or strong yellow green (2.5 GY 7/8), (5 GY 7/8). (b) Lower epidermis—variegated and distinctively characterized by a field with green blotches that tend to concentrate along the margins of the blade. (1) Field background: commonly pale greenish yellow (10 Y 9/4), light greenish yellow (10 Y 9/6), light yellow green (2.5 GY 9/4), (2.5 GY 9/6), (5 GY 9/4), (5 GY 9/6), and/or pale yellow green (2.5 GY 9/2), (5 GY 9/2). (2) Field blotches: commonly light yellow green (5 GY 8/6), (7.5 GY 8/6), (7.5 GY 8/4), moderate yellow green (5 GY 6/4), (7.5 GY 7/6), strong yellow green (5 GY 6/8), (5 GY 7/8), and/or light yellowish green (10 GY 7/4).

Inflorescence form: Simple umbel with minute 5-merous bracts and usually 20–40 flowers in a cluster.

Peduncles:

(*A*) *General.*—Hard, fleshy.

(*B*) *Texture.*—Moderately pubescent.

(*C*) *Size.*—(1) Length: usually 10–25 mm. (2) Diameter: usually 2.5–4 mm. and flaring.

(*D*) *Color.*—Characteristically grayish red (5 R 5/6), (7.5 R 4/6) and/or moderate red (5 R 4/8).

Pedicels:

(*A*) *General.*—Soft, fleshy.

(*B*) *Texture.*—Slightly pubescent with crinkled hairs.

(*C*) *Size.*—(1) Length: usually 15–25 mm. (2) Diamter: usually 1.5–2.5 mm.

(*D*) *Color.*—Characteristically dark pink (2.5 R 6/6), (5 R 6/6).

Flowers:

(*A*) *General.*—Complete, perfect, actinomorphous and 5-merous type flower with hypogynous perianth and alternate sepal-petal and petal-corona segment arrangement.

(*B*) *Size.*—(1) Diameter: usually 14–18 mm.

(*C*) *Calyx.*—(1) General: 5-merous with separate valvate sepals. (2) Texture: (a) Upper epidermis—glabrous and semi-glossy, (b) Lower epidermis—puberulent. (3) Sepal size: (a) Proximal to distal end length—usually about 3 mm. (4) Sepal color: (a) Upper and lower epidermis—characteristically moderate red (2.5 R 5/8), (5 R 4/8) and/or grayish red (5 R 5/6), (7.5 R 4/6).

(D) *Corolla.*—(1) General: 5-merous, valvate and rotate with interpetal basil fusion for about ½ petal length. (2) Petal texture: (a) Upper epidermis—dense velvety pubescence. (b) Lower epidermis—glaborus and waxy. (3) Petal size: (a) Proximal to distal end length—usually about 7 mm. (4) Petal color: (a) Upper and lower epidermis—moderate pink (10 RP 7/6).

(E) *Corona.*—(1) General: 5-merous born-like segments which are adnate to stigma and corolla and crested at their proximal ends. (2) Segment texture: hard, glabrous, smooth and waxy. (3) Segment size: (a) Proximal to distal end length—about 4 mm. (b) Maximum width—about 2.5 mm. (4) Segment color: (a) Proximal end—moderate purplish red (10 RP 4/10) (10 RP 4/8) and merging with distal end color. (b) Distal end—pale yellow green (10 Y 9/2) and merging with proximal end color.

(F) *Androecium.*— (1) General: 5-merous pollinium pairs partially enclosed by expanded translucent parenchymatous translators attached to stigma through corpuscula located between adjacent segments and with pollinia and translators rising above corpuscula and stigma in converging conical arrangement. (2) Pollinium color—vivid yellow (5 Y 8/12).

(G) *Gynoecium.*—(1) General: compound and apocarpous pistil with common stigma. (2) Stigma: (a) General—5-lobed and waxy. (b) Stigma color—pale yellow (5 Y 9/2). (3) Style: lacking. (4) Ovary: (a) General—2-monacarpellate ovularies with axillary placentation of ovules. (b) Size—(1) Length—about 2 mm. (c) Color—grayish purplish red (10 RP 4/10).

Growth rate: vigorous in tropical and semi-tropical enviroments.

The following is a description of a typical plant specimen grown in central Florida under the conditions indicated heretofore.

Age: 11 months from propagation of cutting.
Vine length: 27 cm.
No. of nodes: 18.
No. of fully matured leaves: 26.
No. of immature leaves: 4.
No. of enaryonic leaves: 6.

Stem:

(1) *Diameter.*—Ranges from 4 mm. at about 4 cm. from root end to 3 mm. at about 5 cm. from stem tip.

(2) *Color.*—Moderate red (2.5 R 4/8) at about 5 cm. from stem tip. Dark pink (2.5 R 6/6) at about 12 cm. from stem tip. Pale orange yellow (10 YR 8/4) at about 4 cm. from root end.

Leaves:

(1) *Non-embryonic Petioles.*— (a) Diameter—(1) Immature—2 mm. (av). (2) Mature—3 mm. (av). (b) Length—(1) Immature—ranges from 4 mm. to 6 mm. (2) Mature—ranges from 6 mm. to 9 mm. (c) Color—(1) Immature—light olive (5 Y 5/6), moderate olive brown (2.5 Y 4/4). (2) Mature—light olive (10 Y 5/6) (7.5 Y 5/6), strong yellow green (2.5 GY 6/8), and moderate olive (5 Y 4/4).

(2) *Non-embryonic blades.*—(a) Length—(1) Immature—ranges from 32 mm. to 40 mm. (2) Mature—ranges from 40 mm. to 60 mm. (b) Width (maximum)—(1) Immature—ranges from 16 mm. to 18 mm. (2) Mature—ranges from 20 (a) Border area—predominantly moderate olive green (7.5 GY 4/4) (7.5 GY 4/6) and moderate yellow green (7.5 GY 5/6). (b) Center field background—predominantly light yellow green (2.5 GY 9/4), greenish white (5 GY 9/1) and pale yellow green (2.5 GY 9/2) (5 GY 9/2). (c) Center field blotches—predominantly light yellow green (5 GY 8/6), moderate yellow green (5 GY 7/6) (7.5 GY 7/6) and strong yellow green (5 GY 7/8). (2) Lower epidermis: (a) Field background—predominantly light yellow green (5 GY 9/4, (2.5 GY 9/4) and pale yellow green (2.5 GY 9/2). (b) Field blotches—predominantly light yellow green (5 GY 8/6) (7.5 GY 8/6) (7.5 GY 8/4), light yellowish green (10 GY 7/4) and moderate yellow green (5 GY 6/4) (7.5 GY 7/6).

The following is a description of a typical flower cluster that developed in a plant specimen grown in the central Florida area under the conditions indicated heretofore.

Peduncle:

(1) *Age.*—About 1 year.

(3) *Diameter.*—About 2 mm. (av).

(3) *Diameter.*—About 3 mm.

(4) *Color.*—Grayish red (7.5 R 4/6).

Pedicels:

(1) *Number.*—26.

(2) *Length.*—Range from 18 mm. to 25 mm.

(3) *Diameter.*—About 2 mm. (av.).

(4) *Color.*—Dark pink (5 R 6/6).

Flowers:

(1) *Number.*—26.

(2) *Diameter.*—about 15 mm. (av).

(3) *Calyx.*—(a) Sepal size: about 3 mm. between proximal and distil ends. (b) Sepal color: (1) Upper epidermis—moderate red (5 R 4/8). (2) Lower epidermis—grayish red (5 R 5/6).

(4) *Corolla.*—(a) Petal size: about 7 mm. between proximal and distil ends. (b) Petal color: (1) Upper epidermis—moderate pink (10 RP 7/6).

(2) Lower epidermis—moderate pink (10 RP 7/6).

(5) *Corona.*—(a) Segment size: (1) Proximal to distal end lengths—about 4 mm. (2) Maximum widths—about 2.5 mm. (b) Segment color: (1) Proximal ends—moderate purplish red (10 RP 4/10) (10 RP 4/8). (2) Distal ends—pale yellow green (10 Y 9/2).

(6) *Androcium.*—(a) Pallinium color: vivid yellow (5 Y 8/12).

(7) *Gynoecium.*—(a) Stigma color: pale yellow (5 Y 9/2). (b) Ovary: (1) Size: lengths about 2 mm. (2) Color: grayish purplish red (10 RP 4/10).

I claim:

1. The new distinct variety of the milkweed family substantially as herein shown and described and characterized in particular as to novelty by a growth habit providing speciments which are structurally closely similar in appearance to plant specimens of the Hoya carnosa compacta variety but which are distinguishable therefrom by a combination of the following distinctive characteristics:

(a) a more compact growth habit, (b) lighter appearing stems which in color are characterized by hues which predominantly range from pink to orange yellow in fully matured stems, (c) lighter appearing petioles which in color are characterized by hues which predominantly range from olive to yellow green in fully matured leaves, (d) variegated leaf blades which at the upper epidermis side are distinctively characterized by a green border area that surrounds an albino center field which has green blotches that are lighter in color than the border area and tend to concentrate along the surrounding border area, and which at the lower epidermis side are distinctively characterized by a field with green blotches that tend to concentrate along the margins of the leaf blade, and (e) an inflorescence with a peduncle and sepals that are characteristically grayish red and/or moderate red and with pedicels that characteristically are dark pink in color.

No references cited.

ROBERT E. BAGWILL, Primary Examiner

PO-1050
(5/69)

UNITED STATES PATENT OFFICE
CERTIFICATE OF CORRECTION

Plant
Patent No. 3054 Dated August 10, 1971

Inventor(s) Barnell L. Cobia

It is certified that error appears in the above-identified patent and that said Letters Patent are hereby corrected as shown below:

Column 1, Line 41, delete "taking" and substitute -- taken --;
Column 2, Line 39, delete "(A) Botanic.-Milkweed (Asclepiadaceae) family" and substitute -- (A) General - Caulescent, fleshy, herbaceous. --;
Line 40, delete "(B) Commercial. - Foliage plant." and substitute -- (B) Texture - Copious long hairs. --;

Line 58, delete "enaryonic" and substitute -- Embryonic --;
Column 5, Line 7, after "20" insert -- mm. to 32 mm. (c) Color - (1) Upper epidermis: --;
Line 30, delete "(3) Diameter. - About 2 mm. (av)." and substitute -- (2) Length. - 22 mm. --;
Column 6, Line 9, delete "Pallinium" and substitute -- Pollinium --;
Line 18, delete "speciments" and substitute -- specimens --;

Signed and sealed this 8th day of May 1973.

(SEAL)
Attest:

EDWARD M.FLETCHER,JR.
Attesting Officer

ROBERT GOTTSCHALK
Commissioner of Patents